(12) United States Patent
Murayama

(10) Patent No.: US 6,322,573 B1
(45) Date of Patent: Nov. 27, 2001

(54) ELECTRIC TONGUE CLEANER

(76) Inventor: Ronald K. Murayama, P.O. Box 6599, Laguna Niguel, CA (US) 92607-6599

( * ) Notice: Subject to any disclaimer, the term of this patent is extended or adjusted under 35 U.S.C. 154(b) by 0 days.

(21) Appl. No.: 09/638,350

(22) Filed: Aug. 15, 2000

Related U.S. Application Data

(63) Continuation of application No. 09/042,308, filed on Mar. 13, 1998, now Pat. No. 6,102,923.

(51) Int. Cl.$^7$ ..................................................... A61B 17/24
(52) U.S. Cl. ............................................................ 606/161
(58) Field of Search ..................................... 606/162, 161; D24/147, 146, 148–150

(56) References Cited

U.S. PATENT DOCUMENTS

| | | | |
|---|---|---|---|
| D. 242,744 | 12/1976 | Rendleman et al. | D83/12 |
| D. 253,789 | 12/1979 | Gupta | D24/23 |
| D. 367,707 | 3/1996 | Baker | D24/147 |
| D. 376,695 | 12/1996 | Tveras | D4/104 |
| 1,701,616 | 2/1929 | Gross . | |
| 1,992,770 | 2/1935 | Rathbun | 433/119 |
| 3,477,435 | 11/1969 | Artelli | 128/304 |
| 3,683,924 | 8/1972 | Louie | 128/304 |
| 3,811,447 | 5/1974 | Weber | 128/304 |
| 3,890,964 | 6/1975 | Castanedo | 128/62 R |
| 3,943,592 | 3/1976 | Bhaskar et al. | 15/160 |
| 4,079,478 | 3/1978 | Andrews, Sr. | 15/210 |
| 4,356,585 | 11/1982 | Protell et al. | 15/111 |
| 4,455,704 | 6/1984 | Williams | 15/111 |
| 4,488,327 | 12/1984 | Snider | 15/111 |
| 4,582,059 | 4/1986 | Tiwari | 128/304 |
| 4,610,043 | 9/1986 | Vezjak | 15/111 |
| 4,880,382 | * 11/1989 | Moret et al. | 433/118 |
| 5,061,272 | 10/1991 | Reese | 606/161 |
| 5,217,475 | 6/1993 | Kuber | 606/161 |
| 5,226,197 | 7/1993 | Nack et al. | 15/111 |
| 5,438,726 | 8/1995 | Leite | 15/105 |
| 5,530,981 | 7/1996 | Chen | 15/111 |
| 5,569,278 | 10/1996 | Persad | 606/161 |
| 5,584,690 | 12/1996 | Maassarani | 433/125 |
| 5,772,434 | 6/1998 | Winston | 433/119 |
| 5,947,912 | * 9/1999 | Montagnino | 601/142 |

* cited by examiner

Primary Examiner—Gene Mancene
Assistant Examiner—Eduardo C. Robert
(74) Attorney, Agent, or Firm—Lyon & Lyon LLP

(57) ABSTRACT

An electrically powered device for cleaning the dorsal surface of the tongue, including a handle having a longitudinal axis, and an elongate member extending from the handle and terminating in a cleaning head adapted to reciprocate in a predetermined direction. An electric motor is provided within the handle adapted to operate at a predetermined frequency and thereby reciprocate the elongate member. The cleaning head includes agitation members and one or more cleaning members, such as elongate blades or banks of bristles. The agitation are arranged substantially perpendicular to the predetermined direction of reciprocation, while the cleaning members extend across the width of the cleaning head. The elongate member has a predetermined configuration that is tuned to resonate when reciprocated at a predetermined frequency, preferably within the sonic range, i.e. between about 1,000 and about 20,000 cycles per minute, thereby inducing a resonance action in the cleaning head. The arrangement of the agitation members and the resonance action result in a agitation cleaning effect that loosens plaque from within the surface of the tongue and substantially enhances cleaning thereof.

20 Claims, 3 Drawing Sheets

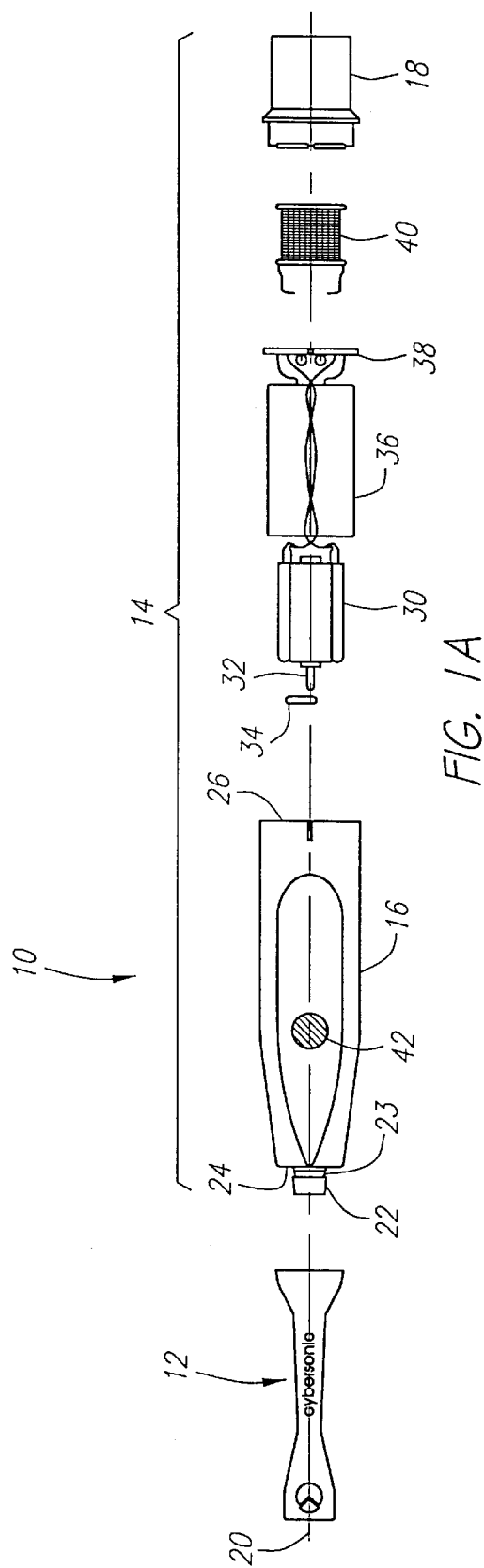
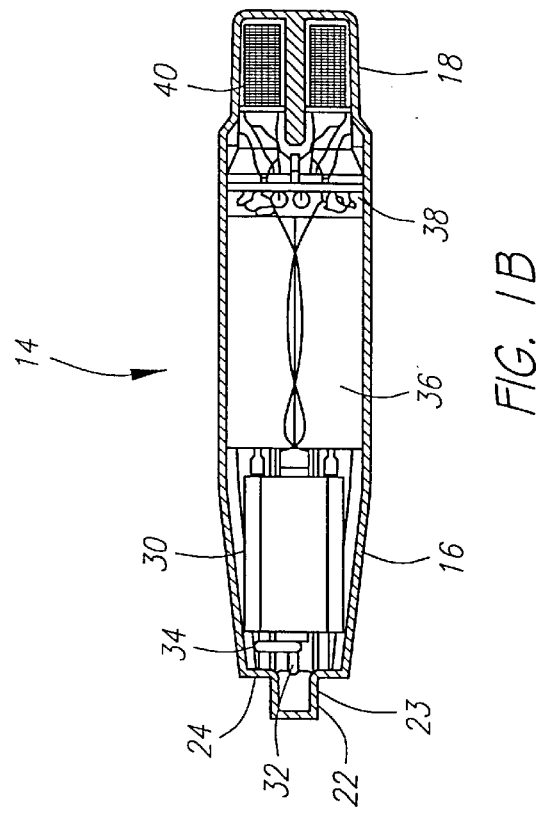
FIG. 1A
FIG. 1B

ELECTRIC TONGUE CLEANER

CROSS REFERENCE TO RELATED APPLICATIONS

This is a continuation U.S. application Ser. No. 09/042,308, filed on Mar. 13, 1998 now U.S. Pat. No. 6,102,923. The priority of the prior application is expressly claimed and its disclosure is hereby incorporated by reference in its entirety.

FIELD OF THE INVENTION

The present invention relates generally to oral hygiene, and more particularly to an electrically powered device for cleaning the surface of the tongue, and most particularly to an electric tongue cleaning device that uses high-speed oscillation to dislodge bacterial plaque and other debris from within the surface of the tongue to enhance the cleaning thereof, and to methods of using such a device.

BACKGROUND OF THE INVENTION

Halitosis or bad breath is a cosmetic problem that afflicts millions of people. The primary source of halitosis is bacteria of the oral cavity, and particularly those that inhabit the dorsal surface of the tongue. Certain kinds of bacteria produce volatile sulfur compounds (VSC's) that are responsible for the most common malodors associated with bad breath. In addition to taste buds, the dorsal or top surface of the tongue also includes papillae, which are microscopic finger-like projections resembling a thick carpet on the surface of the tongue.

The carpet-like structure of the tongue papillae provides a favorable harbor for bacteria to accumulate and propagate between 5 the papillae, thereby often producing a bacterial tongue plaque, which may also include other debris such as food, tobacco byproducts, and salivary residue. The presence of bacterial tongue plaque on and within the surface of the tongue facilitates the production of oral; VSC's, thereby contributing to halitosis or 10 bad breath.

Many methods have been employed to remedy the problem of halitosis often, the odors are simply masked, for example by using flavored breath mints or candies, mouth drops, aerosol sprays, lozenges or chewing gum. These products employ aromatic oils or compounds, such as wintergreen or peppermint, to overpower and thereby mask the malodors of halitosis, as well as food-related odors, such as garlic or onions. Alternatively, mouth washes and mouth rinses may be used. These products usually include anti-bacterial agents, such as alcohol, or a combination of chemical agents and aromatic compounds, such as oil of wintergreen. Anti-bacterial or chemical agents may kill bacteria to consequently prevent them from producing VSCIs, while aromatic components simply mask any prevailing odors, and give the user a feeling of refreshment.

Another method widely used to eliminate halitosis involves cleaning the tongue. Besides using chemical agents, two basic categories of tongue cleaning devices are often used, namely tongue brushes and tongue scrapers. Tongue brushes have head and bristle designs, e.g. wide heads and/or low profile bristles, that are specifically adapted for brushing the tongue, although sometimes toothbrushes may simply be used for this purpose. Tongue scrapers are long, narrow blades of metal or plastic, which are manually pulled over the dorsal surface of the tongue. Some tongue scrapers may resemble a common disposable razor, except with a plastic edge or ridge in place of the razor blade. other scrapers are a long, narrow blade which is held by a user on both ends of the blade and then pulled or scraped over the dorsal surface of the tongue.

One of the problems often encountered with conventional scrapers or brushes is that they have difficulty cleaning the relatively inaccessible areas of the tongue surface, particularly those areas adjacent to the base of the papillae. Because of the relatively slow speeds at which these devices are operated, they generally only clean the outermost surface of the tongue papillae. The bristles or blades provide poor access into the "carpet" of the papillae to loosen debris therein, and consequently conventional devices may not effectively remove the bacterial tongue plaque located within the surface of the tongue, i.e. between or adjacent to the base of the tongue papillae, which contributes substantially to halitosis.

Accordingly, there is a need for more effective devices and methods for removing bacterial tongue plaque and/or treating halitosis.

SUMMARY OF THE INVENTION

The present invention is directed to an electrically powered device for cleaning the surface of the tongue. In a preferred embodiment, the device includes an electrically, powered handle having a longitudinal axis, and an elongate member extending axially from the handle and terminating in a cleaning head adapted to reciprocate in predetermined direction. The cleaning head includes a plurality of agitation members for loosening debris within the surface of the tongue, and/or one or more cleaning members for removing debris from the surface of the tongue. An electric motor is provided within the handle adapted to operate at a predetermined frequency and thereby reciprocate the elongate member in the predetermined direction at the predetermined frequency.

Preferably, the agitation members are arranged on the cleaning head substantially perpendicular to the predetermined direction of reciprocation, and the cleaning member extends across the cleaning head substantially perpendicular to the longitudinal axis of the handle. One or more of the agitation members and/or the cleaning member may be an elongate blade or an elongate bank of bristles.

The elongate member preferably is a tongue cleaning attachment that may be detachably mounted on the handle. The tongue cleaning attachment preferably has a predetermined configuration that is tuned to resonate when reciprocated at a predetermined frequency, preferably within the sonic range, i.e. between about 1,000 and about 20,000 cycles per minute, thereby inducing a resonance action in the cleaning head.

In a preferred embodiment of the handle, an eccentric counterweight is attached to the motor, the counterweight being adapted to produce sonic vibrational energy. The sonic energy may be transmitted to the tongue elongate member, i.e. through the handle and the elongate member, thereby reciprocating the cleaning head.

During use, the cleaning head is placed in contact with the surface being cleaned, preferably the dorsal surface of the tongue. The cleaning head is reciprocated, preferably at speeds of between about 2,000 and about 40,000 strokes per minute, whereby the agitation members engage the dorsal surface to 10 dislodge debris therefrom. The cleaning head is manually directed along the surface of the tongue, whereby the cleaning member cleans the surface thereof.

Thus, an important feature of the present invention is that the cleaning head includes a plurality of agitation members and one or more cleaning members. The agitation members are oriented on the cleaning head substantially perpendicular to the direction of reciprocation to serve an agitating function to loosen bacterial tongue plaque from within the surface of the tongue, while the cleaning members are oriented preferably across the width of the cleaning head to remove the loosened bacterial plaque and other debris from the surface of the tongue, and thereby substantially reducing the production of VSC's that may contribute substantially to halitosis.

Accordingly, a principal object of the present invention is to provide an electrically powered device for cleaning the tongue, and particularly for loosening plaque and other debris within the surface of the tongue.

Other objects and features of the present invention will become apparent from consideration of the following description taken in conjunction with the accompanying drawings.

BRIEF DESCRIPTION OF THE DRAWINGS

FIG. 1A is an exploded view of a preferred embodiment of a tongue cleaning device in accordance with the present invention.

FIG. 1B is a cross-sectional view of an assembled handle of the tongue cleaning device of FIG. 1A.

BRIEF DESCRIPTION OF THE PREFERRED EMBODIMENTS

Figure 2A:
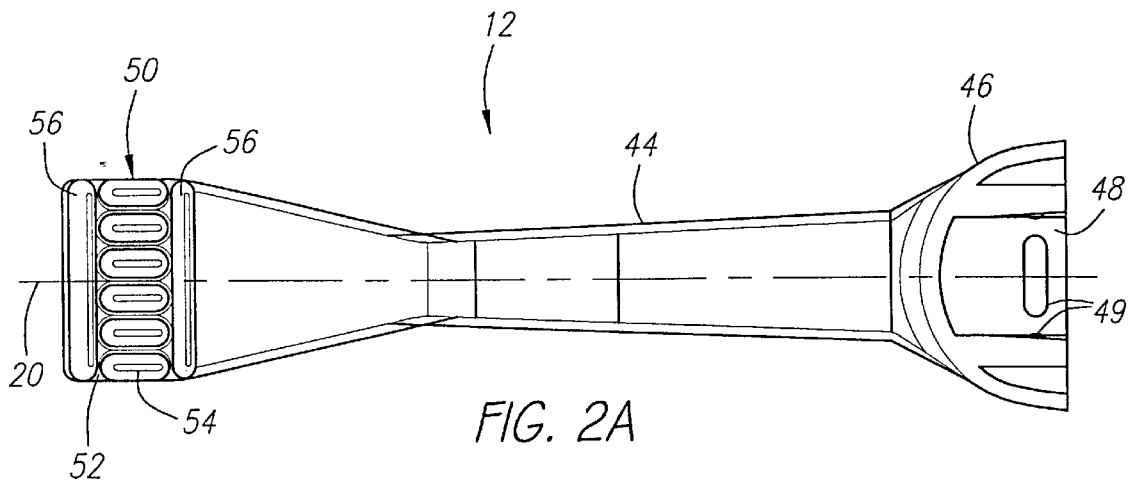
FIG. 2A is an enlarged bottom view of the tongue cleaning attachment shown in FIG. 1A.
Figure 2B:
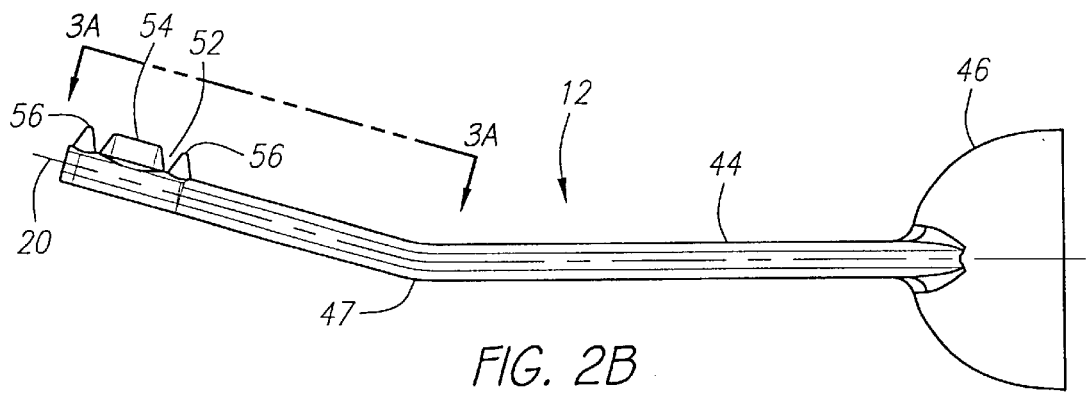
FIG. 2B is an enlarged side view of the tongue cleaning attachment shown in FIG. 1A.
Figure 2C:
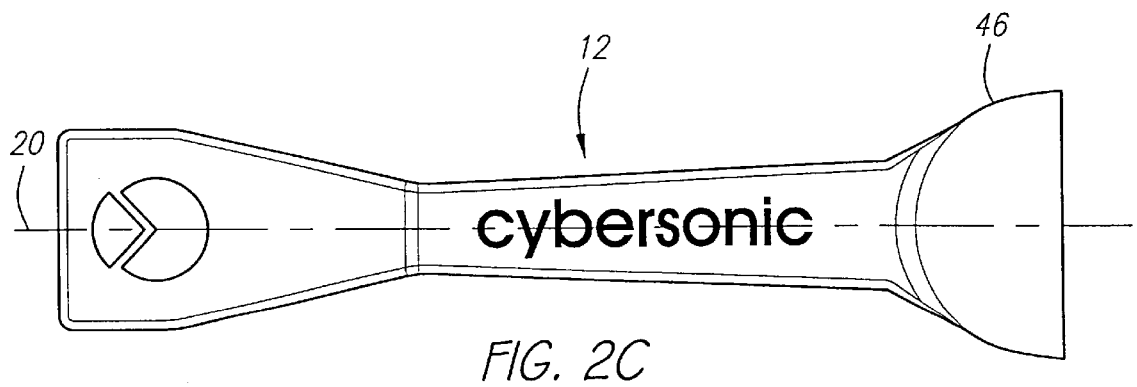
FIG. 2C is an enlarged top view of the tongue cleaning attachment of FIG. 1A.
Figures 3A, 3B:
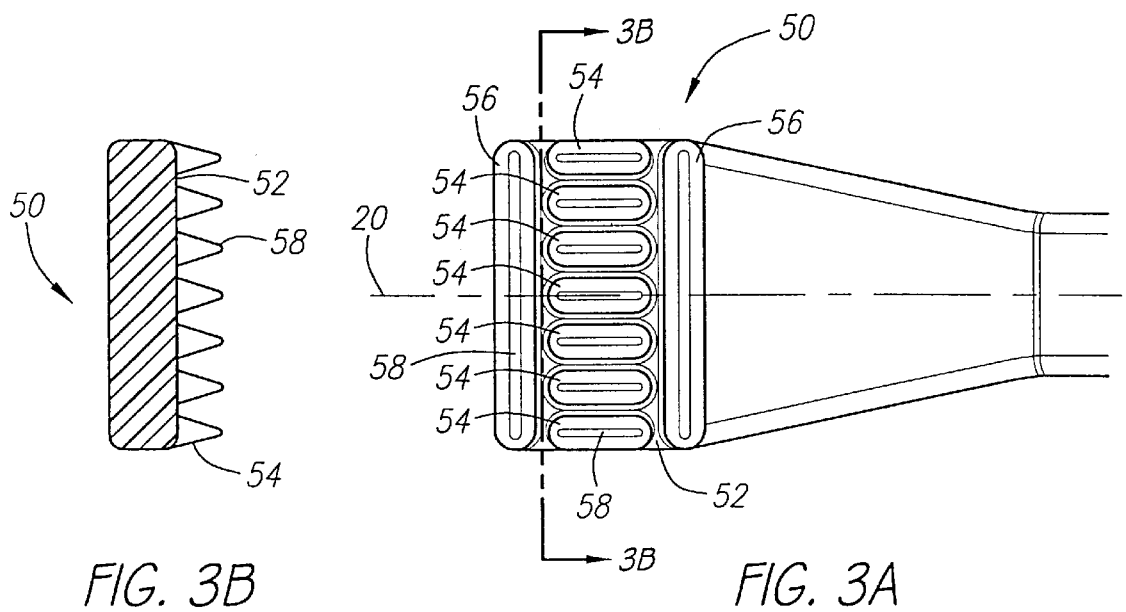
FIG. 3A is a detail of the cleaning head of the tongue cleaning attachment of FIG. 2A.
FIG. 3B is a cross-section of the cleaning head of FIG. 3A, taken along line B—B.

Turning now to the drawings, FIGS. 1, 2A–2C and 3A–3B show a preferred embodiment of an electrically powered tongue-cleaning device 10 in accordance with the present invention. The device 10 includes two main components, namely a tongue cleaning attachment 12 and an electrically powered handle 14. The handle 14 includes a hollow casing 16 and an end piece 18, both preferably made of polymeric plastic, defining a longitudinal axis 20. The casing 16 has a connector hub 22 formed on its distal end 24 onto which the tongue cleaning attachment 12 may be detachably mounted, and has an open proximal end 26 which is substantially enclosed when the end piece 18 is attached to the casing 16.

An electric motor 30 is provided within the handle 14, which has an output shaft 32 onto which a disc 34 or other counterweight is eccentrically mounted. Power for the motor 30 is stored and supplied by batteries 36, which are also located within the handle 14. An electric circuit board 38 is located between the batteries 36 and a recharging coil 40, which enables recharging of the device 10 by induction in a conventional manner. An on/off switch assembly 42 is provided on the casing 16 and is coupled to the circuit board 38, thereby controlling the flow of electrical current from the batteries 36 to the motor 30. Alternatively, switch providing a plurality of speed settings may be provided instead of the simple on/off switch shown.

With particular reference to FIGS. 2A–2C and 3A–3B, the tongue cleaning attachment 12 is an elongate member 44 preferably formed from nylon or polymeric plastic, including a connector 46 on one end for detachably connecting the tongue cleaning attachment 12 to the handle 14, and a cleaning head 50 on its other end. The connector 46 preferably includes a recessed area 48 into which the hub 22 on the handle 14 may be securely received, thereby anchoring the tongue cleaning attachment 12 to the handle 14 simply by friction and/or by interlocking tabs 49 and slots or grooves 23. The tongue cleaning attachment 12 may include a bend 47 between the cleaning head 50 and the connector 46 for ergonomic purposes, e.g., to facilitate access to the back of the tongue. As will be explained further below, the tongue cleaning attachment 12 preferably has a predetermined configuration, e.g., a predetermined size, shape and weight, that are selected to "tune" the tongue cleaning attachment 12 to resonate at a predetermined frequency, preferably matched to the frequency of the vibrational energy produced by the disc 34 and motor 30 in the handle 14.

The cleaning head 50 includes a substantially flat surface or face 52 from which extend a plurality of elongate ridges or blades 54, 56. The blades 54, 56 are preferably formed directly on the face 52 of the cleaning head 50, although alternatively they may be separate attachable components. Preferably, the blades 54, 56 have substantially rigid edges 58, which are sufficiently rounded to prevent cutting or other damage to the surface of the tongue. In the preferred embodiment shown, a first set of blades 54, called agitation blades, are arranged on the face 52 substantially parallel to the longitudinal axis 20. A second set of blades 56, called scraping or cleaning blades, are also arranged on the face 52, but extend substantially perpendicular to the longitudinal axis 20.

During use, the tongue cleaning attachment 12 is first selected and connected to the handle 14. The cleaning head 50 is directed into the user's mouth and the face 52 is placed into contact with the dorsal surf ace of the tongue (not shown) The switch 42 is moved to the on position, which activates the motor 30, thereby causing the output shaft 32 and consequently the disc 34 to rotate at a predetermined frequency. Because the disc 34 is mounted eccentrically, it produces vibrational energy at the predetermined frequency.

The circuit board 38 and switch assembly 42 regulate the frequency of the motor 30 and disc 34, but the frequency may also be limited by the motor 30, and the specific weight, shape and size of the disc 34. Preferably, these parameters are preselected such that the disc 34 rotates at sonic frequencies, typically between 1,000 and 20,000 cycles per minute (cpm), and preferably between 7,000 and 18,000 cpm. Thus, the disc 34 produces sonic energy, i.e. vibrational energy in the sonic range.

The handle 14 absorbs the resulting sonic energy, and consequently transmits the sonic energy to the tongue cleaning attachment 12 connected to the hub 22 on the handle 14. The sonic energy is then transmitted through the tongue cleaning attachment 12, thereby causing the cleaning head 50 to reciprocate, i.e., move back and forth, as it engages the surface of the tongue. Generally, the cleaning head 50 reciprocates in a one-to-one ratio with the vibrations of the disc 16, i.e., each cycle of the disc 16 produces one cycle, or two strokes (one to each side), of the cleaning head 50.

Preferably, the sonic energy creates "resonance action" in the cleaning head 50, which substantially enhances the cleaning of the tongue. The phenomenon of resonance action is related to the physical configuration of a body being vibrated, and consequently will only occur under very specific scientifically determinable conditions. In order for resonance action to occur, all elements of the body must be in tune and in harmony with one another. The given material composition, design, size, shape, and weight of the body dictate its inherent "natural resonance frequency." At this frequency, a relatively small amount of vibrational energy applied to the body will result in a relatively large amplitude vibration or reciprocation of the body being vibrated.

With respect to the present invention, resonance action only occurs when the tongue cleaning attachment 12 and its cleaning head 50 are vibrated at their natural resonance frequency. When vibrated at this frequency, for example by the sonic energy created by the disc 34, this produces a relatively large amplitude vibration, or reciprocating movement, of the cleaning head 50, which facilitates cleaning of the tongue. Thus, the tongue cleaning attachment 12 must be tuned to the frequency of the sonic energy produced by the disc 34, either by adjusting the speed of the motor 30 and consequently the frequency of the sonic energy produced by the disc 34, or preferably by initially selecting a configuration for the tongue cleaning attachment 12 that provides a natural resonance frequency that is matched to the predetermined frequency of the sonic energy produced by the disc 34.

Preferably, the physical configuration of the tongue cleaning attachment 12, i.e. its size, shape and/or weight, is predetermined such that the cleaning head 50 reciprocates in a plane substantially parallel to the longitudinal axis 20 and/or substantially parallel to the face 52 of the cleaning head 50. Stated differently, the cleaning head 50 preferably reciprocates side-to side in a direction substantially perpendicular to the longitudinal axis 20 such that the face 52 remains substantially parallel to and engaging the surface of the tongue being cleaned. Most preferably, with the connector 46 substantially anchoring the tongue cleaning attachment 12 to the handle 14, the tongue cleaning attachment, 12 behaves similarly to a cantilevered beam, causing the cleaning head 50 to swing or sweep back and forth in an arc defined by an axis of rotation substantially perpendicular to the longitudinal axis 20.

In addition, the arrangement of the blades 54, 56 on the cleaning head preferably results in the resonance action producing an "agitation cleaning effect" that helps dislodge bacterial tongue plaque and/or other debris from deep within the surface of the tongue, i.e. from between the papillae, to enhance cleaning and substantially reduce halitosis. For this to occur, at least some of the blades, i.e. the agitation blades 54, are preferably oriented such that they extend along the face 52 of the cleaning head 50 in a direction substantially perpendicular to the direction of reciprocation of the cleaning head 50. For example, in the preferred embodiment shown, because the cleaning head 50 reciprocates or swings side-to-side, the long dimension of the agitation blades 54 extends along the face 52 substantially parallel to the longitudinal axis 20. Thus, the edges 58 of the agitation blades 54 reciprocate back and forth over the surface of the tongue, vibrating the surface of the tongue to loosen bacterial tongue plaque and other debris therein.

In addition, some of the blades, i.e. the scraping blades 56, are arranged substantially perpendicular to the direction in which the tongue-cleaning device 10 is directed over the surface of the tongue, i.e. substantially perpendicular to the longitudinal axis 20. Thus, as the cleaning head is manually moved over the surface of the tongue, the edges 58 of the scraping blades 56 remove debris from and clean the surface.

Thus, an important feature of the present invention is that the cleaning head 50 includes a plurality of agitation members and one or more scraping or cleaning members, such as the blades 54, 56 respectively. The agitation members are oriented on the face 52 of the cleaning head 50 substantially perpendicular to the direction of reciprocation to serve an agitating function to loosen bacterial tongue plaque, while the cleaning members are oriented across the width of the cleaning head to remove the loosened bacterial tongue plaque and other debris from the surface of the tongue. This combination of agitation and scraping members results in a more effective device for cleaning the surface of the tongue than previously available using conventional scraping or brushing implements.

Figures 4A, 4B:
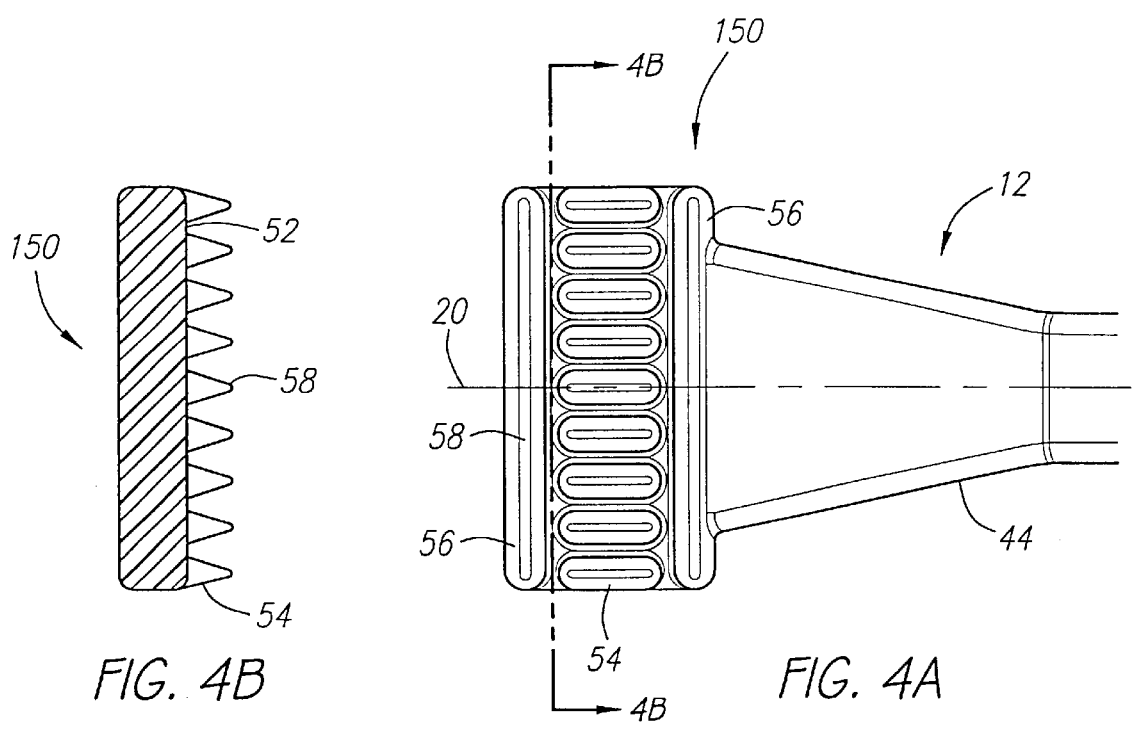
FIG. 4A is a detail of an alternative embodiment of a cleaning head in accordance with the present invention.
FIG. 4B is a cross-section of the cleaning head of FIG. 4A, taken along line B—B.

The cleaning head 50 may include a variety of shapes and agitating or cleaning members arranged thereon to facilitate cleaning of the surface of the tongue. For example, as shown in FIGS. 4A and 4B, the cleaning head 150 may have a wider cross-section for engaging a wider region of the tongue, and reducing the number of times that the cleaning head 150 must be directed over the surface of the tongue. Alternatively, instead of blades, the cleaning head may include one or more sets of bristles (not shown). Similar to the blades previously described, the bristles would be arranged in elongate or linear banks, each bank performing similar to a single blade, i.e. either providing an agitation member or a cleaning member.

Similar to the blade description above, agitation bristles would preferably be arranged in linear banks that are substantially perpendicular to the direction of reciprocation, while cleaning bristles would be arranged substantially perpendicularly to the longitudinal axis of the handle.

In other configurations of the electric tongue-cleaning device in accordance with the present invention, the cleaning head may be substantially permanently attached to the handle or may be formed as a unitary extension of the handle, for example by extending the hub (not shown). In addition, a plurality of tongue cleaning attachments with different arrangements or combinations of blades and/or bristles may be provided with a single handle to provide an interchangeable system for enhancing the cleaning of the tongue.

In further alternatives, a variety of handle assembles or mechanical systems may be provided to oscillate or reciprocate the cleaning head in a variety of reciprocation patterns (not shown). For example, in a first alternative, the cleaning head may be reciprocated in a circular motion pattern having an axis of rotation that is substantially perpendicular to the longitudinal axis of the device. This pattern may be achieved using an electric motor in the handle connected to a series of gears and/or shafts for mechanically moving the tongue cleaning attachment directly. This would require that the agitation members on the cleaning head be arranged in a circular pattern and/or that the long dimension of the agitation members be substantially perpendicular to the arc of motion of the cleaning head to maximize the agitation cleaning effect.

In a second alternative, the cleaning head may be reciprocated in a linear side-to-side pattern in a direction substantially perpendicular to the longitudinal axis of the handle, also using an electric motor coupled to the cleaning head by gears and/or shafts. Similar to the preferred embodiment described above, the long dimension of the agitation members would then preferably be arranged substantially parallel to the longitudinal axis of the handle.

In a third alternative, the cleaning head may be reciprocated in a back and forth pattern substantially parallel to the longitudinal axis of the handle, also by using an electric motor connected to the cleaning head by gears and/or shafts. In this embodiment, the long dimension of the agitation members would be arranged substantially perpendicular to the longitudinal axis of the handle.

In a fourth alternative, the cleaning head may be reciprocated in a sweeping or arcing pattern having an axis of rotation substantially parallel to the longitudinal axis of the handle. This pattern may be achieved using an electric motor connected to the cleaning head by gears and/or shafts, or using circular electromagnets and ferrous motors connected to the cleaning head by a series of gears and/or drive shafts. In this embodiment, the long dimension of the agitation members would also be arranged substantially perpendicular to the longitudinal axis of the handle.

Finally, in a fifth alternative, the side-to-side arcuate pattern of reciprocation associated with the preferred embodiment shown in the figures and described above may also be achieved using an electric motor connected to the cleaning head by gears and/or shafts, or using electromagnets and ferrous motors connected by a series of swinging levers, gears and or drive shafts, rather than using vibrational energy.

Thus, an important feature of the present invention is to provide an electric tongue cleaning device that provides a substantially increased number of cleaning strokes as compared with manual devices. At rates of between about 2,000 and about 40,000 strokes per minute, a tongue-cleaning device in accordance with the present invention applies substantially more cleaning energy to the tongue than manual devices. Further, the high-speed reciprocating action of the cleaning head produces an agitating action on the papillae of the tongue to enhance the device's cleaning efficacy, which is fundamentally different from simple mechanical scraping.

In addition, while a cleaning head in accordance with the present invention may be mechanically connected directly to a motor to produce a reciprocating cleaning action as described above, it is preferred that vibrational energy, particularly in the sonic range, be used to induce reciprocation. This substantially simplifies the electric cleaning device, eliminating multiple mechanical parts, such as gears or shafts, which are required in direct mechanical devices and which often fail during use.

Further, in accordance with the present invention, it is most preferred to use harmonic resonance by tuning the cleaning head to the frequency of the sonic energy produced within the handle. The harmonic resonance, as previously described, enhances the agitation cleaning effect obtained when the specially arranged agitation members of the cleaning head engage the surface of the tongue, to help loosen plaque and other debris from within the surface of the tongue, and thereby enhance the cleaning of the tongue.

While the invention is susceptible to various modifications, and alternative forms, specific examples thereof have been shown in the drawings and are herein described in detail. It should be understood, however, that the invention is not to be limited to the particular forms or methods disclosed, but to the contrary, the invention is to cover all modifications, equivalents and alternatives falling within the spirit and scope of the appended claims.

What is claimed is:

1. A device for cleaning the dorsal surface of a tongue, comprising:
   an electrically powered handle defining a longitudinal axis, and comprising a motor configured for producing vibrational energy; and
   an elongate cleaning member extending axially from the handle and terminating in a cleaning head configured for reciprocating in a plane substantially parallel to the longitudinal axis of the handle in response to the vibrational energy, the cleaning head having a face including a plurality of elongate agitation members and one or more cleaning members extending therefrom in a predetermined arrangement.

2. The device of claim 1, wherein the elongate agitation members are arranged substantially perpendicular to a direction of reciprocation of the cleaning head.

3. The device of claim 1, wherein the elongate agitation members are disposed substantially parallel to the longitudinal axis.

4. The device of claim 1, wherein the one or more elongate cleaning members are disposed substantially perpendicular to the longitudinal axis.

5. The device of claim 1, wherein each of the elongate agitation members comprises at least one of an elongate blade and a row of bristles.

6. The device of claim 1, wherein each of the one or more elongate cleaning members comprises an elongate scraping member.

7. The device of claim 6, wherein the elongate scraping member comprises an elongate blade terminating in a substantially rigid edge.

8. A tongue cleaning attachment for scraping the dorsal surface of a tongue, the tongue cleaning attachment comprising:
   an elongate member having first and second ends and defining a longitudinal axis therebetween, the first end being connectable to an electrically powered handle adapted to produce vibrational energy, the second end being configured to reciprocate when vibrational energy is transmitted thereto from the first end; and
   a cleaning head on the second end for cleaning the surface of the tongue, the cleaning head including a face comprising an elongate agitation member thereon for loosening debris within the surface of the tongue and an elongate scraping member thereon for removing debris from the surface of the tongue.

9. The tongue cleaning attachment of claim 8, wherein the elongate agitation member is oriented substantially perpendicular to a direction of reciprocation of the cleaning head.

10. The tongue cleaning attachment of claim 8, wherein the agitation member comprises a plurality of elongate agitation blades oriented substantially perpendicular to a direction of reciprocation of the cleaning head.

11. The tongue cleaning attachment of claim 8, wherein the elongate agitation member is disposed substantially parallel to the longitudinal axis.

12. The tongue cleaning attachment of claim 8, wherein the elongate agitation member comprises at least one of an elongate blade and a row of bristles.

13. The tongue cleaning attachment of claim 8, wherein the scraping member is disposed substantially perpendicular to the longitudinal axis.

14. The tongue cleaning attachment of claim 8, wherein the elongate scraping member comprises an elongate blade terminating in a substantially rigid edge.

15. A device for cleaning the dorsal surface of a tongue, comprising:

an electrically powered handle having a longitudinal axis, and comprising a motor, the motor configured to produce sonic range vibrational energy; and a tongue cleaning member extending axially from the handle and terminating in a cleaning head, the cleaning head including a face having a plurality of elongate cleaning members extending therefrom, the cleaning head having a predetermined configuration tuned to resonate when subjected to the sonic range vibrational energy produced by the motor thereby inducing a resonance action in the cleaning head.

16. The device of claim 15, wherein the sonic range vibrational energy produced by the counterweight causes the cleaning head to reciprocate at between about 2,000 and about 40,000 strokes per minute.

17. The device of claim 15, wherein the cleaning members comprise a plurality of blades, at least one of the blades comprising an agitation blade for loosening debris within the surface of the tongue, and at least one of the blades comprising a scraping blade for removing debris from the surface of the tongue.

18. The device of claim 17, wherein the agitation blade is oriented substantially perpendicular to a direction of reciprocation of the cleaning head.

19. The device of claim 17, wherein the agitation blade comprises a plurality of elongate agitation blades oriented substantially perpendicular to a direction of reciprocation of the cleaning head.

20. The device of claim 15, wherein the cleaning members comprise a plurality of elongate agitation members for loosening debris within the surface of the tongue, and an elongate scraping member for removing debris from the surface of the tongue.

* * * * *